US00PP10339P

United States Patent [19]

Larsen

[11] Patent Number: Plant 10,339

[45] Date of Patent: Apr. 21, 1998

[54] OSTEOSPERMUM PLANT NAMED 'SUNNY GIRL'

[75] Inventor: Bjarne Larsen, Odense, Denmark

[73] Assignee: Paul Ecke Ranch, Encinitas, Calif.

[21] Appl. No.: 698,337

[22] Filed: Aug. 15, 1996

[51] Int. Cl.[6] ..... A01H 5/00

[52] U.S. Cl. ..... Plt./68.1

[58] Field of Search ..... Plt./68.1

[56] References Cited

PUBLICATIONS

UPOV-ROM Plant Variety Database 'Sunny Girl', Osteospermum, PBR OST 00003, 1991.

*Primary Examiner*—Howard J. Locker
*Assistant Examiner*—Melissa L. Kimball
*Attorney, Agent, or Firm*—Arnold, White & Durkee

[57] ABSTRACT

A new and distinct cultivar of Osteospermum named 'Sunny Girl', particularly characterized by its spreading growth habit with excellent pinkish-purple and white bi-color flower color, early flowering and dark green foliage, and suitability to 6 inch pots, and 8 and 10 inch hanging basket cultures.

1 Drawing Sheet

BACKGROUND OF THE PLANT

The present invention relates to a new and distinct cultivar of plant known as Osteospermum. The new cultivar is known by the cultivar name 'Sunny Girl', and was developed by the inventor Bjarne Larsen in Odense, Denmark in 1988. A new cultivar was obtained by crossing two identified seedlings from the breeding program of Bjarne Larsen.

Asexual reproduction by terminal (stem tip) cuttings taken by me or under my supervision at Kernen Greenhouse in Odense, Denmark, has shown that the unique features of this new Osteospermum are stabilized and are reproduced true to type in successive propagations.

The following characteristics distinguish the new Osteospermum from both its parent varieties and other cultivars of this general type known and used in the floriculture industry:

1. A unique pinkish-purple and white bi-color flower with a blue center.
2. A spreading compact growth habit.
3. Early flower response.
4. Well suited for 6" pots, nursery containers, and hanging baskets.

'Sunny Girl' is similar to the unpatented cultivar 'Alm. Rosa'. 'Sunny Girl' shows stronger, deeper rose nuances as compared to 'Alm. Rosa' and lighter color toward the ray flower center. Leaves of 'Sunny Girl' are more broadly obovate in form as compared to 'Alm. Rosa'.

Chart A compares 'Sunny Girl' with 'Sunny Silvia' which is the most closely comparable plant to the knowledge of the inventor. 'Sunny Silvia' is described and illustrated in co-pending U.S. plant patent application, Ser. No. 08/698,339. No known relation exists between 'Sunny Silvia' and 'Sunny Girl'.

Plants described in Chart A illustrate comparison of three plants in one hanging basket.

CHART A

| Characteristic | 'Sunny Silvia' | 'Sunny Girl' |
|---|---|---|
| Plant Height (above the pot) | 32 cm | 32 cm |
| Plant Width | 48 cm | 67 cm |
| Flower Head Diameter | 9 cm | 8.8 cm |
| Flower Color - mature ray | RHS 78B fading | RHS 80C fading |

-continued

CHART A

| Characteristic | 'Sunny Silvia' | 'Sunny Girl' |
|---|---|---|
| petals | to nearly white at proximal end | to RHS 155B at proximal end |

DESCRIPTION OF PHOTOGRAPH

The accompanying colored photograph is a side perspective view of the new cultivar, showing color as true as it is reasonably possible to obtain in a colored reproduction of this type.

DESCRIPTION OF THE PLANT

The following is a detailed description of my new Osteospermum cultivar based on plants grown under commercial practice in Encinitas, Calif. Three rooted cuttings were transplanted into 26 cm (10 inch) hanging baskets on Dec. 11, 1995. Plants were pinched on Jan. 2, 1996, and received plant growth regulator on January 16 and 31. The values, measurements and observations noted below were taken from plants in bloom on Feb. 29, 1996, and continued in flower through April 1996.

On Apr. 10, 1996, I observed a plant in a 26 cm hanging basket 32 cm tall. This basket had three branched plants with an overall height of 43 cm and an overall width of 67 cm. Each plant had 5 strong branches, originating from within 1.5 cm of the soil line, for a total of 15 branches. Each branch was approximately 27 cm long terminating in a flower. At observation, there were 39 flowers open and 111 flower buds in various stages of development. Three secondary shoots subtend the terminal flower from the top 3 nodes on the primary shoot. These secondary shoots also terminated in a flower.

Color references are made to The Royal Horticultural Society Colour Chart (R.H.S.), except where general terms of ordinary dictionary significance are used.

The Plant

Origin: Seedling from cross pollination.

Parentage: Cross between seed parent of unknown origin and pollen parent of unknown origin.

Classification:

*Botanical.—Osteospermum ecklonis.*

*Common name.*—Osteospermum.

*Cultivar name.*—'Sunny Girl'.

Asexual reproduction:

A. *Cutting type.*—Vegetative shoot tip with stems approximately 3 cm long and developing to 4–5 cm after 28 days in propagation.

B. *Time to initiate roots.*—8–10 days at 20° C.; nicely developed root mass in 21–28 days.

C. *Rooting habit.*—Numerous, fibrous adventitious roots from the stem base.

D. *Growth.*—Standard growth retardant application for 'Sunny Girl' includes 1–2 applications of Daminozide/Butanedioic acid mono (2.2 dimethylhydrazide) at a rate of 2,500 ppm. Applications are made as foliar sprays. Growth retarding chemicals generally reduce height by ⅓.

Plant description:

A. *Form.*—Symmetrical, low growing perennial shrub, with good branching characeristics after pinching, giving the plant a full appearance.

B. *Habit of growth.*—Vigorous, spreading habit, producing approximately 12 leaves per stem and terminating in flowers. After the initial flowers form, typically 3 subordinate axillary shoots develop from the nodes of the uppermost leaves producing additional flowering shoots. This process is continuous so long as night temperatures remain below 16° C.

C. *Foliage description.*—1. Leaf shape: Obovate with acuminate tip and attenuate leaf base. 2. Leaf blade size: Mature leaves 6.6 cm long and 3.5 cm wide. 3. Petiole length: Approximately 2 cm in length. 4. Leaf margin: Slightly sinuate with 3–7 pointed lobes on either side of the leaf blade. 5. Leaf texture: Slightly undulant and twisted at the tip. (i) Upper surface: Slightly pubescent with short, white trichomes evenly distributed throughout the leaf surface. (ii) Under surface: Glabrous. 6. Leaf color: Dark green. (i) Upper surface: Near R.H.S. 147A. (ii) Under surface: Near R.H.S. 146A. 7. Venation: Palmately branched with a single predominate light green colored mid-vein on the upper surface. 8. Foliage fragrance: Characteristic Osteospermum plant fragrance, particularly notable when foliage is wet.

Flower description: Daisy type composite flower with disk and ray florets that close at night and open in the morning. The ligulate petal of the ray floret subtends the pistil. The disk florets contain male flower parts. Florets on the flower heads are imperfect with pistillate ray florets and staminate disk florets.

A. *Flowering habits.*—Flowering is determinate with one primary flower at the end of a long 19–26 cm pedicel (on open flowers). Each pedicel had approximately 3–5 leaflets on the proximal end of the pedicel. A secondary flower arises from the base of the primary pedicel.

B. *Natural flowering season.*—Flowering occurs primarily February through October in the northern hemisphere. Initiation occurs after a cool temperature vernalization (10–17° C.). Floriferousness may wane during hot summer days in temperate climates. Plants initially potted from rooted cuttings, pinched two weeks later, then maintained at temperatures of 10°–12° C. for four weeks thereafter growing for seven weeks at temperatures of about 18° C. will flower in approximately 13 weeks.

C. *Flower buds.*—Flower buds develop successively on secondary branches, reaching a size of 2.3 cm long and 1.4 cm wide prior to opening.

D. *Flowers borne.*—Singularly 9 cm above the plant canopy.

E. *Quantity of flowers.*—Secondary flowers occur progressively around the primary flower so that tight buds to mature flowers are visible at the same time.

F. *Flower head.*—1. Number of florets: 15–16 ray florets and numerous disk florets, making up a flower disk approximately 1.2 cm in diameter. 2. Shape: Narrow linear florets with obtuse to acute tips and acute bases. Floret approximately 4 cm long and 1 cm wide. 3. Color: Ray florets are light purple-violet and white near the base and lower peripheral edges; disk florets are violet-blue. (i) Upper surface of ray florets: Near R.H.S. 80C, fading to white near base; whiter than R.H.S. 155B. (ii) Under surface of ray florets: Alternating stripes near R.H.S. 76A and 76D. (iii) Disk florets: Near R.H.S. 86B. 4. Surface: (i) Upper surface of ray florets: Glabrous. (ii) Under surface of ray florets: Glabrous but pubescent near the base. 5. Inflorescence size: Up to 8.8 cm in diameter. 6. Flower fragrance: None.

G. *Reproductive organs.*—1. Stamens: Short stamens emerge on outermost disk florets and progress toward the center. 2. Anther: Each disk floret has 1 stamen terminating in a 5-part anther. 3. Pollen: Copious and golden yellow. 4. Stigma: Bipartite. 5. Styles: Short, approximately 2 mm long and purple. 6. Ovary: Inferior to florets and green in color.

H. *Resistance.*—1. Frost resistance: Withstands light frost. 2. Diseases: Resistant to most root, stem, foliage and flower diseases.

What is claimed:

1. A new and distinct cultivar of Osteospermum plant named 'Sunny Girl' as illustrated and described.

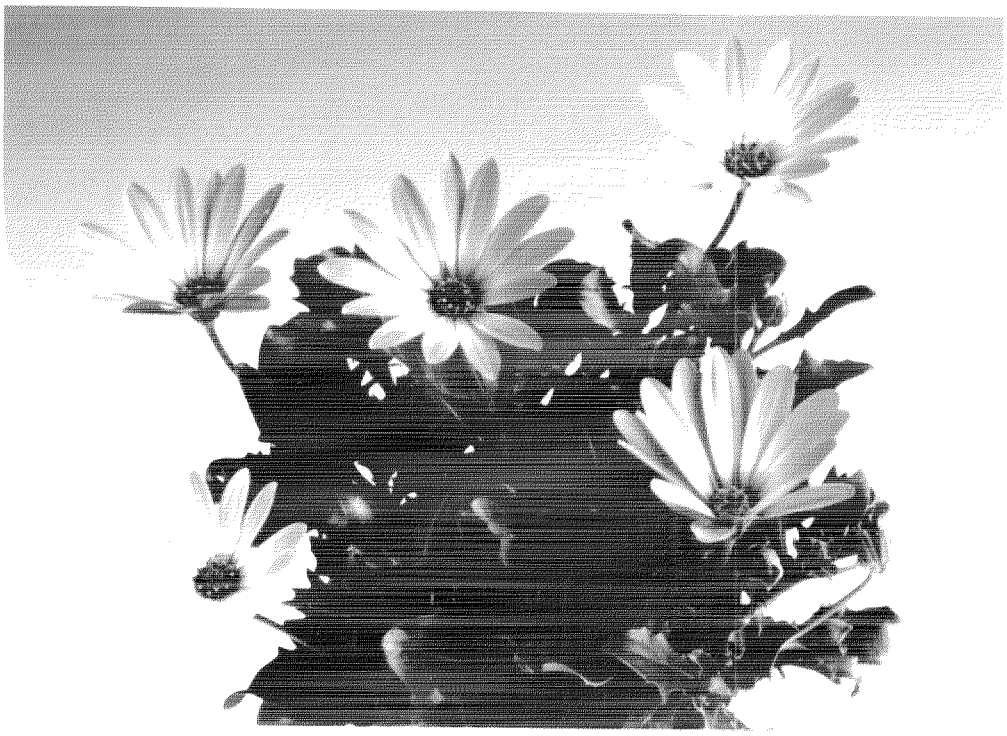

* * * * *